United States Patent [19]
Price

[11] Patent Number: 5,176,694
[45] Date of Patent: Jan. 5, 1993

[54] EYE SPUD

[76] Inventor: James A. Price, 26 Windwood Hill, Jackson, Tenn. 38305

[21] Appl. No.: 637,176

[22] Filed: Jan. 3, 1991

Related U.S. Application Data

[63] Continuation-in-part of Ser. No. 416,032, Oct. 2, 1989, abandoned.

[51] Int. Cl.$^5$ ............................................. A61B 17/50
[52] U.S. Cl. .................................................... 606/162
[58] Field of Search ...................... 606/131, 161, 162; 604/1

[56] References Cited

U.S. PATENT DOCUMENTS 1,263,942  4/1918  Schroeder .
1,272,170  7/1918  Ziegler .
1,305,442  6/1919  Carr .
4,600,008  7/1986  Schmidt ............................. 128/357

FOREIGN PATENT DOCUMENTS 91281  11/1921  Switzerland .
304020  1/1929  United Kingdom .

OTHER PUBLICATIONS

Mueller "The Surgical Armamentarium" pp. 1000, 1004–1005 (1980).

Primary Examiner—Michael H. Thaler
Attorney, Agent, or Firm—Luedeka, Hodges, Neely & Graham

[57] ABSTRACT

An eye spud designed for use in removing foreign objects embedded in or adhering to the surface of the eye globe with minimal risk of infection or physical damage of the eye globe.

6 Claims, 3 Drawing Sheets

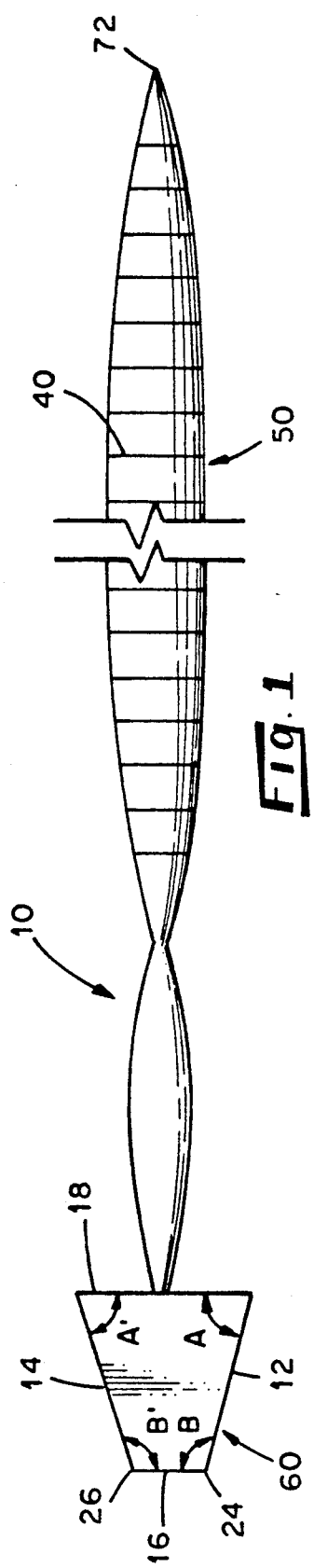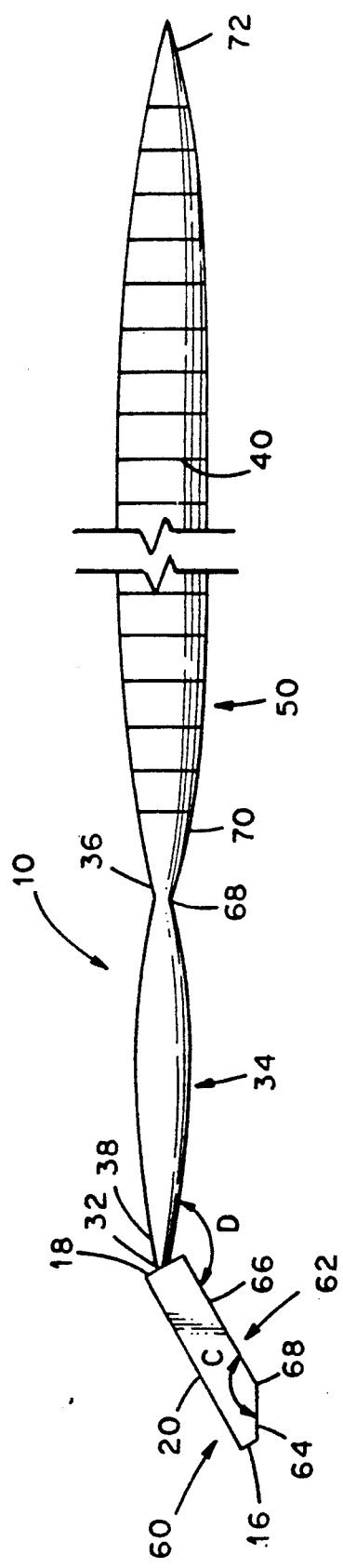

EYE SPUD

This application is a continuation-in part application of copending application Ser. No. 07/416,032, filed Oct. 2, 1989, now abandoned, entitled EYE SPUD.

FIELD OF THE INVENTION

This invention relates to the field of ophthalmology and specifically to an eye spud for use in the removal of foreign bodies from the surface tissue of the eye globe.

BACKGROUND

Most foreign objects entering the eye are readily flushed out by the natural defensive mechanism of tears from the lacrimal glands. Those foreign objects which are not readily flushed by tears require other means of removal. When a foreign object either adheres to or becomes embedded in the corneal or conjunctival layer of the eye globe such that removal by flushing the eye with fluid is ineffective, removal by a mechanical device such as a very sharp disposable hypodermic needle or other rigid ophthalmological instrument is commonly employed. Among the problems associated with the use of mechanical instruments for removing foreign objects from the eye are (1) effectiveness of the instrument while avoiding undue physical damage to the tissue of the eye and (2) sterility of the instrument so that the chance of infection of the delicate corneal tissue is kept to a minimum.

The prior art has addressed these problems in a number of different ways which are either not as effective in removing foreign objects or considerably less safe methods than the present invention. U.S. Pat. Nos. 1,272,270; 1,263,942 and 1,305,442 show typical prior art instruments that depend on a flexible tip that must be moistened so that the foreign substance clings to the instrument and not the eye. None of these instruments are designed to effectively and safely get under an embedded foreign object to safely dislodge it from the delicate eye tissue. In fact, i.e. U.S. Pat. No. 1,305,442, one of these instruments consists of a rubber coated wire that is inserted in the eye which has the possibility of seriously damaging the eye if the wire breaks and comes through the soft rubber coating.

In U. K. Pat. No. 304,020 there is shown an instrument designed to get under the foreign object and dislodge it instead of having the foreign object removed because it adhered more strongly to the instrument than to the eye. This instrument consists of a pointed blade which is said to be effective in getting under the embedded foreign object by reason of loosening the embedded object with the blade and using a quill or feather on the other end of the instrument to sweep the object off the eye. The problem with this instrument is that because of its pointed blade design, it may easily puncture the eyeball by means of a misjudgment by the user as to the pressure that must be applied to dig under the foreign body sufficiently to safely lift and remove it from the eye.

A still further prior art instrument disclosed in U.S. Pat. No, 4,600,008 contemplates removal of a foreign body by means of a loop of thread that may be drawn over the surface of the eye underneath the eyelid to dislodge the foreign body but which is not abrasive enough to scratch the eye surface. If a foreign substance has adhered to the eye or become embedded in its tissue so that it cannot be removed by flushing the eye with a saline solution, a loop of the type suggested in this prior art device may not be sufficient to get under the foreign object and dislodge it regardless of the pressure that can be applied to the eyelid of a closed eye while the loop is being drawn over the surface tissue of the eye.

SUMMARY OF THE INVENTION

The eye spud of the present invention comprises a handle to which there is attached a uniquely designed flat substantially rigid and non-yielding, unitary blade portion of generally trapezoidal geometry suitable to be urged underneath a foreign object lodged in the eye globe to dislodge such object from the eye globe without penetrating or permanently damaging the eye globe. Substantial width and a slight tapering of the thickness of the blade adjacent its outboard leading edge are provided to achieve a shovel or chisel type effect and enhance the ability of the blade to substantially depress the surface of the eye globe and move beneath the foreign body without damage to the tissue by the blade itself. The side edges of the trapezoidally shaped blade are relatively dull and relatively wide to permit distribution of the pressure applied to the eye globe in dislodging the foreign object to avoid gouging or penetration of the eye globe. The blade, however, is designed to be tilted to cause one corner of the substantially rigid blade to serve a gouging or digging function. In a preferred embodiment, the blade portion of the instrument is oriented at an angle with respect to its handle portion to provide for ease and precision of manipulation of the instrument and better visualization of the operative field by the surgeon or other medical specialist.

OBJECTS OF THE INVENTION

It is an object of the present invention to provide an efficient and safe device for dislodging and/or removing a foreign body embedded or adhering to the corneal tissue of the eye.

It is another object of the invention to provide a device for use in dislodging and/or removing a foreign body embedded or adhering to the corneal tissue of the eye without puncturing the eye globe.

BRIEF DESCRIPTION OF THE DRAWINGS

FIG. 1 is a side elevational view of one embodiment of an instrument in accordance with the present invention.

FIG. 2 is a top view of the instrument depicted in FIG. 1.

DETAILED DESCRIPTION OF THE INVENTION

Figure 3A:
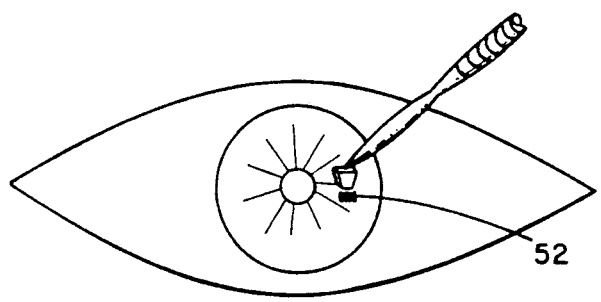
FIGS. 3A, 3C and 3E are diagrammatic representations of three phases of a procedure for removing an embedded object from an eye and employing the instrument disclosed herein.

Referring now to the drawings, and in particular to FIG. 1, an apparatus for safely and effectively removing an embedded or adhering foreign object from the eye is indicated generally at 10. The apparatus 10 comprises a rigid handle member, indicated generally at 50, and a blade member, indicated generally at 60. In the depicted embodiment, a neck member 34 is disposed between the blade member and the handle member. The handle member 50 is designed for ready grasping in the hand and for ease of manipulation of the blade member 60 to safely engage a foreign object in the eye and remove it by scooping underneath it or by digging into the corneal layer if necessary.

The preferred blade of the present instrument is substantially rigid and non-yielding. Such construction is of importance in that in use, the blade of the instrument may be urged into contact with the eye globe with an applied pressure sufficient to physically depress the eye globe in the region adjacent to a foreign object lodged in the eye globe and thereby permit the blade to be urged and/or moved under such foreign object for extracting the same from the eye globe. The blade member 60, which is located at the distal end of the instrument, is of generally trapezoidal shape with sides 12, 14, 16 and 18. The base or proximal side 18 of the trapezoid has the two sides 12 and 14 extending from the ends of the proximal side 18 at acute angles A and A' with respect to the base. In the depicted embodiment, the angles A and A' are equal but other suitable angles may be employed. The two sides 12 and 14 each terminate at the opposing ends of the distal side 16 of the trapezoidal shaped blade member forming obtuse angles B and B' with respect to the distal side 16. In the depicted embodiment the distal side 16 is parallel to the proximal side 18 of the blade member. Where the sides 12 and 14 of the blade member meet the top of the trapezoid 16, a sharp, i.e., essentially non-radiused, corner is formed at each junction 24 and 26 respectively. All four sides of the trapezoid 12, 14, 16 and 18 are relatively blunt, i.e. non-cutting, but side 16 is tapered as noted herein.

With reference to FIG. 2, the top of the blade member 20 is a relatively flat, smooth planar surface. The bottom side of the blade member 62, however, consists of two planar surfaces 64 and 66 each of which is relatively flat and smooth, and which are joined at a linear interface 68. The planar surface 66 which is at the proximal end of the blade is parallel to the top side 20. The planar surface 64 is disposed at an obtuse angle C in relation to the planar surface 66. This configuration of the bottom side of the blade, comprising two planar surfaces 64 and 66 joined at the linear interface 68 at an obtuse angle with respect to one another, allows for a tapering of the thickness of the blade member towards the distal side end of the blade 16 thereby enhancing the ability of this edge of the blade to slide under a foreign object that is embedded in the eye globe.

In a preferred embodiment, the critical measurements of the blade member are as follows. With reference to FIG. 1, the length of the blade as measured from the proximal side 18 to the distal side 16 is about 2.0 mm. No side is longer than about 2.5 mm. The distal side 16 of the blade member is about 0.8 mm long. With reference to FIG. 2, the thickness of the distal side 16 of the blade member at its most distal edge does not exceed about 0.1 mm, and the length of taper of the thickness of the blade member as measured from the linear interface 68 is about 0.75 mm.

With reference to FIGS. 1 and 2, the depicted embodiment includes, in addition to the blade member and handle member, a neck member 34. The neck member is generally linear and elongate with two opposing ends 38 and 68 and is disposed between the blade member 60 and the handle member 50. The neck member is connected to the proximal side 18 of the blade member in approximately the center 32 of the proximal side 18. The neck and blade members preferably are oriented to one another at an obtuse angle D for ease of manipulation of the instrument. In the depicted embodiment, this obtuse angle D is 135°. The opposite end 68 of the neck member is connected to one end of the handle member 70 at junction 36. The neck member, while not an essential element of the apparatus, is included to spatially separate the handle member from the blade member so that the user's hand is at an adequate distance from the eye for the user to see to safely manipulate the apparatus. In one suitable embodiment the optimal length of the neck member is approximately 4.0 mm.

The handle member 50 of the apparatus is a relatively thin, linear, elongate member with two opposing ends 70 and 72. The distal opposing end 70 is attached to the neck member 68 of the spud in the depicted embodiment at junction 36. If the neck member is not present, the handle member 50 is attached directly to the blade member 60 in the center 32 of the proximal side 18 of the blade member. In a preferred embodiment the handle member 50 of the apparatus is serrated 40 along its length to provide the user with a suitable gripping surface.

Whereas the present instrument may be fabricated of a metal such as stainless steel, in a preferred embodiment of the present instrument, the entire instrument is formed of a plastic material, such as polyethylene, and preferably high density polyethylene. Injection molding is the preferred method of manufacture, but it is recognized that other suitable methods of manufacture may be employed. In any event, the method of manufacture and material of construction chosen should provide a handle and blade, and neck where included, that in combination define a unitary instrument of sufficient rigidity and stiffness as permits the user to grasp the instrument in his hand and apply sufficient pressure through the instrument, and especially the blade, to physically depress the surface of the eye globe by an amount sufficient to enable the blade to be moved underneath a foreign object lodged in the eye globe and serve to lift the foreign object from the eye globe. To this end, the blade is to be unitary, as opposed to multiple elements such as bristles on a brush or the like, and non-yielding, as opposed to a resilient or yielding sponge or the like. As noted hereinbefore, the blade further is provided with at least one sharp corner distally of the blade. Such corner is intended to permit it to be placed in contact with the eye globe with a minimum of the surface area of the blade initially in contact with the eye globe for depressing the eye globe at such location of contact, and as the corner of the blade is pressed further, and harder, into contact with the eye globe, an increasingly larger area of the corner of the blade engages the eye globe, thereby permitting greater pressure to be exerted by the blade corner against the eye globe for physically depressing the eye globe even further, but without the corner of the blade physically rupturing the eye globe. To this end, the preferred sharp corner at each end of the distal edge of the blade possesses essentially zero radius. Any material radius on such corner reduces the effectiveness of the corner for its intended purpose, and a substantial radius on such corner can render the corner inoperable for the intended purpose as set forth above. As noted, the configuration of the blade with a generally trapezoidal shape and dull sides permits the user to effectively and efficiently remove an embedded or adhering foreign object from the eye without penetration of the eye globe. The relatively wide distal side 16 of the blade member 60 permits distribution of the pressure applied to the eye in dislodging the foreign object. The sharp corners at the junctions 24 and 26, however, allow the user of the apparatus to dig into the corneal or conjunctival tissue and get underneath a foreign object embedded in the corneal or conjunctival layer if the distal side 16 of the blade is not sufficiently sharp to do this. This procedure of digging into the eye surface tissue is a safe use of the apparatus because of the unique trapezoidal configuration of the blade member. As greater pressure is applied by the user to the apparatus, the obtuse angles B and B' at the distal side of the blade member, quickly reduce the pressure per square inch applied to the eye globe as the corner begins to penetrate deeper into the corneal or conjunctival tissue. The reduction in applied pressure occurs because of the increasingly larger surface area placed in contact with the corneal or conjunctival tissue as the blade is urged against the eye globe.

Figure 3B:
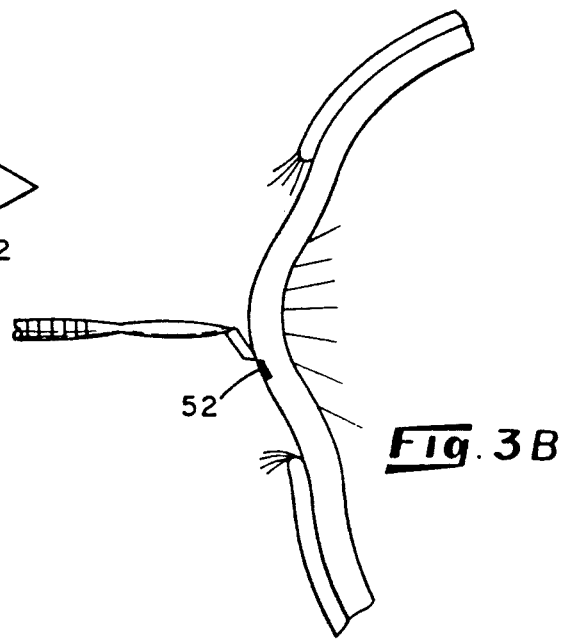
FIGS. 3B, 3D and 3F are side views of the representations of FIGS. 3A, 3C and 3E respectively.
Figure 3C:
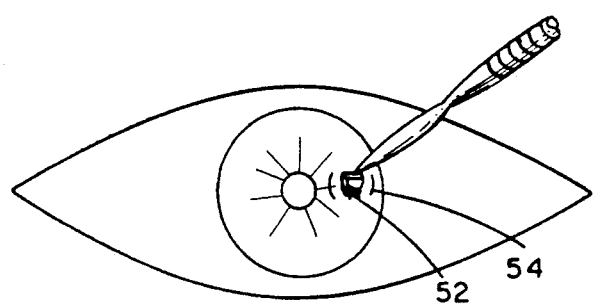
Figure 3D:
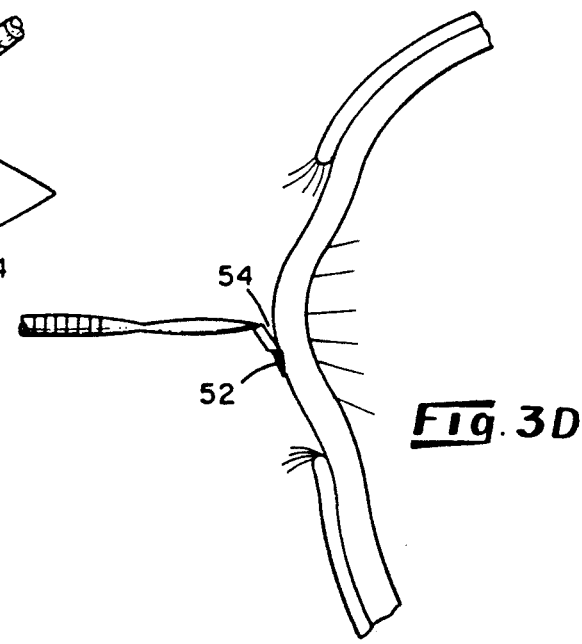
Figure 3E:
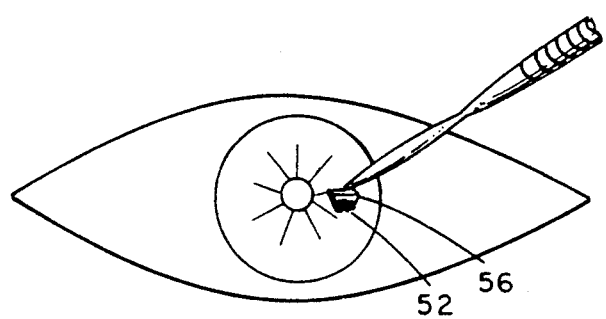
Figure 3F:
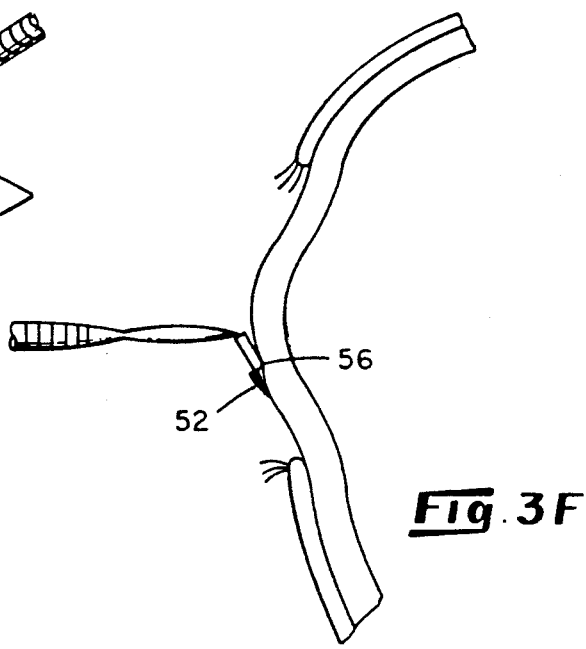
Figure 3G:
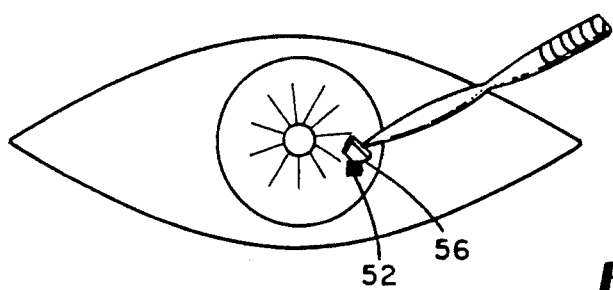
FIG. 3G is a diagrammatic representation of the corner of the instrument being employed to dig beneath a particularly well entrenched object in the corneal tissue of the eye globe.

With reference to FIGS. 3 A–F, in implementation of the apparatus, the distal side of the blade member 16 is placed with the top side 20 facing u and substantially the entire length of the distal side 16 in contact with the eye tissue. The leading side edge 16 is positioned immediately to the side of the embedded or adhering foreign object 52. The user then applies slight pressure to dimple or depress the resilient corneal tissue 54 immediately adjacent to the foreign object and then urges the blade underneath 56 the foreign object by placing the top side 20 in contact with the eye to scoop the object from the eye with the dull distal side 16 of the blade member.

If the foreign object is so enmeshed in the corneal tissue that the use of the non-cutting, flat distal side 16 of the blade member is ineffective, the user may employ a sharp corner of the blade member to dig into the corneal or conjunctival tissue to free the foreign object from the eye. After partially loosening the foreign object with the sharp corners of the instrument, the user can employ the flat distal side 16 of the blade member to scoop underneath the foreign object as described above.

I claim:

1. An eye spud for use in the removal of foreign objects either embedded in or adhering to the corneal or conjunctival eye tissue comprising:

unitary, substantially rigid and non-yielding blade means, said blade means being substantially planar and of generally trapezoidal geometry having opposite substantially flat, smooth surfaces and having one of its parallel side edges longer than the other of its parallel side edges, the shorter of the two parallel side edges of said trapezoidal blade being exposed for contact with said foreign object with a force sufficient to materially depress the eye tissue adjacent to the foreign object without deleterious penetration of said corneal or conjunctival tissues, and handle means secured to said blade at a location on the longer of the two parallel side edges of said trapezoidal blade suitable for grasping to effect manipulation of said spud, and the side edges of the blade means are sized so that no side edge thereof exceeds about 2.5 mm in length.

2. The eye spud of claim 1 wherein said handle is elongated and the plane occupied by said blade is oriented at an obtuse angle with respect to the longitudinal axis of said elongated handle.

3. The eye spud of claim 2 wherein said obtuse angle is about 135°.

4. The eye spud of claim 1 wherein the margin of said shorter side edge of said blade is tapered to provide a non-cutting edge of a thickness suitable to readily pass under a foreign object as such side edge is urged into contact with the eye tissue with a force sufficient to depress the eye tissue adjacent to the foreign object without effecting further injury to the eye tissue by the spud.

5. The eye spud of claim 1 wherein the shorter side edge of said blade defines at least one defined corner with at least one other side edge of said blade, said corner being essentially non-radiused.

6. The eye spud of claim 1 wherein the shorter side edge of said blade has a minimum thickness of about 0.1 mm.

* * * * *